United States Patent [19]

Walther et al.

[11] Patent Number: 4,528,175
[45] Date of Patent: Jul. 9, 1985

[54] PRODUCTION OF CHROMIUM (III) COMPOUNDS

[75] Inventors: James F. Walther, Skaneateles, N.Y.; John I. Choi, Worthington, Ohio

[73] Assignee: Allied Corporation, Morris Township, Morris County, N.J.

[21] Appl. No.: 442,550

[22] Filed: Nov. 18, 1982

[51] Int. Cl.³ ............................................. C01G 37/00
[52] U.S. Cl. .................................. 423/492; 423/305; 423/419 R; 423/472; 423/544
[58] Field of Search ........... 423/305, 492, 544, 419 R, 423/472

[56] References Cited

U.S. PATENT DOCUMENTS

| | | | |
|---|---|---|---|
| 1,379,578 | 5/1921 | Mooney | 423/544 |
| 2,524,803 | 10/1950 | Iler | 423/492 |
| 2,841,541 | 7/1958 | Smith | 423/492 |
| 2,928,723 | 3/1960 | Perrin et al. | 423/492 |
| 3,305,303 | 2/1967 | Hartford et al. | 23/87 |
| 3,309,172 | 3/1967 | Hartford et al. | 23/87 |

FOREIGN PATENT DOCUMENTS

| | | | |
|---|---|---|---|
| 0848470 | 9/1960 | United Kingdom | 423/492 |
| 0475346 | 10/1972 | U.S.S.R. | 423/492 |
| 0582205 | 11/1977 | U.S.S.R. | 423/492 |
| 0648522 | 2/1979 | U.S.S.R. | 423/544 |
| 0715480 | 2/1980 | U.S.S.R. | 423/544 |
| 0814852 | 3/1981 | U.S.S.R. | 423/305 |

Primary Examiner—Howard S. Williams
Assistant Examiner—Terryence Chapman
Attorney, Agent, or Firm—Richard C. Stewart, II

[57] ABSTRACT

A process of preparing chromium (III) compounds from chromate and/or dichromate salts by forming a mixture of such salts, an acid, water and a reducing agent. Additional acid is added to the mixture which is then cooled selectively precipitating the salt of the anion of the acid and the cation of the chromate and/or dichromate salts which is separated from the solution containing the desired chromium (III) compound.

19 Claims, No Drawings

PRODUCTION OF CHROMIUM (III) COMPOUNDS

BACKGROUND OF THE INVENTION

1. Field of the Invention

This invention relates to a process for the manufacture of chromium (III) compounds from chromate and/or dichromate salts. More particularly, this invention relates to a process for manufacturing such chromium (III) compounds which are essentially free of cations of the chromate and/or dichromate salts.

2. Description of the Prior Art

In recent years, the expanding use of chromium (III) compounds have made these materials of increasing importance. For example, chromium chloride has found utility as a precursor in the manufacture of catalysts and organic compounds of chromium. Similarly, methods have been developed whereby chromium metal may be produced from high purity chromic chloride. The development of NASA's Redox Energy System based on the use of chromic chloride has spurred interest for new inexpensive methods of preparing this compound.

A number of methods for producing chromium (III) compounds, as for example, chromic chloride have been proposed. However, these compounds, and particularly chromic chloride have remained materials which in the past have been prepared with considerable difficulty and at great expense, even on a laboratory or limited pilot plant scale. For example, in one such method for preparing chromic chloride, this material is prepared by passing chlorine gas over ferrochrome or chromium metal at high temperature. However, this process suffers from several defects the most significant of which is that it is very inefficient which results in high expenditures of time, money and man-power.

Other high cost, inefficient processes for preparing chromic chloride involve the use of chromic oxide or chromic acid as the starting materials. In one such process described in U.S. Pat. No. 3,309,172, chromic chloride is prepared by reacting chromic oxide, carbon monoxide and chlorine gas in the presence of an inert particulate material at elevated temperatures. In another such method described in U.S. Pat. No. 3,305,303, chromic chloride is prepared by reacting chromic oxide with chlorine and carbon. It is disclosed in the literature that chromic chloride may also be prepared by either reducing chromic acid with methanol in the presence of hydrochloric acid or by reacting chromic oxide with hydrochloric acid. These prior art processes which involve the use of chromic oxide or chromic acid as the starting materials suffer from a number of inherent defects, chief of which is that the cost of producing the desired product is so great that only minor amounts of the desired product can be used economically and then only in a narrow class of specific situations. The increased cost results from the need to convert chrome ore into the required chromic acid and/or chromic oxide precursors. The production of chromic acid and chromic oxide from chrome ore involves a roasting and leaching operation to convert the ore into sodium chromate, i.e. yellow liquor; acidification of sodium chromate with sulfuric acid to provide a sodium bichromate solution, followed by crystallization and drying of the resultant solid to provide anhydrous sodium bichromate; and reduction of sodium bichromate with carbon or sulfur to provide chromic oxide or combination of sodium bichromate with sulfuric acid to yield chromic acid.

It is apparent that the more desired and economical, both time, equipment and cost-wise route to chromium (III) compounds would be directly from the chrome ore, or directly from sodium chromate or sodium dichromate thereby avoiding the expensive, time consumming chrome ore conversion steps. However, heretofore, none of these prior art processes have been used to prepare chromic chloride either because of an inability to separate the desired chromium (III) compounds from impurities, primarily sodium cations, or because of the prohibitorily high time, cost, manpower and equipment expenditures required for such separation.

SUMMARY OF THE INVENTION

In accordance with this invention, there is provided a process for preparing chromium (III) salts of the formula:

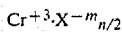

$$Cr^{+3} \cdot X^{-m}{}_{n/2}$$

from chromate and/or dichromate salts, said chromium (III) salts being substantially free of cations of said chromate and/or dichromate salts, wherein:

X is a univalent, divalent or trivalent organic or inorganic anion;

m is 1, 2 or 3; and n is 2 when m is 3, n is 3 when m is 2, and n is 6 when m is 1; said process comprises the steps of:

(A) forming a reaction mixture of comprising one or more chromate and/or dichromate salts, water, a reducing effective amount of a reducing agent and at least a stoichiometric amount of an acid of the formula $H_mX^{-m}$ thereby reducing all or a portion of said chromium species in the +6 state to the +3 state;

(B) cooling said reaction mixture thereby selectively precipitating substantially all salt of said one or more chromate and/or dichromate counter-ion and the anion of said acid from said reaction mixture; and (C) separating said precipitated salt of step (B) from said reaction mixture thereby forming an aqueous solution of $Cr^{+3} \cdot X^{-m}{}_{n/2}$ substantially free of said To form solid $Cr^{+3} \cdot X^{-m}{}_{n/2}$, additional process steps can be employed which comprise removing water from the solution of step (C), and cooling the resulting solution until $Cr^{+3} \cdot X^{-m}{}_{n/2}$ substantially free of cations of the one or more chromate and/or dichromate salts precipitates therefrom.

DESCRIPTION OF THE PREFERRED EMBODIMENTS

In the first step of the process of this invention, chromium in the +6 state present in chromate and/or dichromate salts is reduced to the +3 state by reaction with a reducing effective amount of a suitable reducing agent in the presence of water and an acid species of the formula $H_mX^{-m}$.

As used herein, "chromate and/or dichromate salts" are any salts which contain chromate and/or dichromate species which are totally or partially soluble in water. Illustrative of such salts are chromate and/or dichromate salts of alkali earth metals, as for example sodium chromate, sodium dichromate, potassium chromate, potassium dichromate, and the like. Also exemplary of such useful chromate and/or dichromate salts are salts of alkaline earth metals as for example, barium chromate, barium dichromate, calcium chromate, calcium dichromate, magnesium chromate, magnesium dichromate, strontium chromate, strontium dichromate and the like. Preferred for use in the process of this invention are salts of alkali metal and alkaline earth metals. Particularly preferred for use are the salts of alkali earth metals, with the salts of sodium and potassium being most preferred.

As used herein "a suitable reducing agent" is any reducing agent which is capable of reducing chromium in the +6 state to the +3 state under such conditions. Illustrative of useful and conventional reducing agents are methanol, ethanol, n-propanol, hydrochloric acid, hydrazine, hydrogen gas, formaldehyde, formic adid, carbon monoxide, peroxide, sodium borohydride, hydroxylamine and other like reducing agents known to be capable of reducing chromium in the +6 state to chromium in +3 state. Preferred reducing agents are those whose oxidation reaction products will not contaminant the reaction product. Illustrative of such preferred reducing agents are those agents whose oxidation reaction products are gases, such as methanol, formaldehyde, formic acid, carbon monoxide, peroxide and the like. The particularly preferred reducing agent for use in this invention is methanol. In addition to the reducing agent, various reduction catalysts can be added to the reaction mixture to enhance reaction kinetics. Such catalysts are well known to those skilled in the art and include such materials as silver chloride, lead chloride and noble metals such as platinum and palladium.

The reduction is carried out with a reducing effective amount of the reducing agent. As used herein, a "reducing effective amount" is an amount which is capable of reducing all or a portion of the chromium in the +6 state present in the reaction mixture into the +3 state. In the preferred embodiments of the invention, substantially all chromium (+6) is reduced to chromium (+3), and and in such embodiments a quantity of reducing agent sufficient to accomplish same is employed. As is apparent to those of skill in the art, such amount will vary with the type of reducing agent employed, and will depend on the stiochiometry of the particular reduction reaction. In the particularly preferred embodiments, at least a stiochiometric amount of the reducing agent will be employed, and in the most preferred embodiments a slight excess of the agent will be used to allow for reducible impurities in the reaction mixture which may react with the reducing agent to ensure essentially complete reduction. In those embodiments of the invention in which the oxidation product of the selected reducing agent will not contaminate the final product, i.e. methanol, formic acid, peroxide and the like, and in which the unreacted reducing agent can be removed from the product twofold, threefold, fourfold and like excesses of the agent can be used.

The reduction step is also carried out in the presence of water and an acid species of the formula:

wherein m is as described hereinabove. The purpose of this acid species is two-fold. Some reduction reactions are pH dependent, and the protons provided by the above referenced acid species adjust the pH to obtain optimum reaction kinetics. The second function of the species is to provide a counter ion for the chromium +3 reaction product and for the inert sodium cation. An amount of the acid sufficient to perform both of these functions is referred to herein as "a stiochiometric amount". Thus, if the intended reaction product is chromic sulfate, sulfuric acid would be the acid of choice and an amount sufficient to perform both functions would be added. Similarly, if chromic chloride is the desired reaction product, hydrochloric acid would be the acid of choice, in a stiochiometric amount. All of the acid can be added at the beginning of the process to perform both functions, or sufficient acid can added as required. For example, in the conduct of the process of this invention, sufficient acid to adjust the pH of the reduction reaction mixture can be added at the beginning of the process and after completion of the reduction reaction, an amount of the acid sufficient to provide the counter-ion can be added. Alternatively, an amount of the acid sufficient to accomplish both functions can be added prior to the reduction reaction, or even during the reduction reaction. In the preferred embodiments of the invention the acid is added as required. An amount of acid sufficient to adjust the pH of the reaction mixture is added initially, and on completion of the reduction reaction, acid identical to that employed in the reduction step, or a chemical species which is capable of forming such acid in situ is added to the mixture preferably at ambient temperature, about i.e., 0° C. to about 35° C., in an amount such that the mixture will contain an amount of the anion of the acid equal to or greater than the amount of $Cr^{+3}$ and other cations in the mixture. While not necessarily anhydrous, the acid preferably does not contain excessive amounts of water. Thus, in these preferred embodiments the so that water content of the reaction mixture is not increased so as to prevent the preferential crystallization of substantially all of the chromate and/or dichromate counter ion and the anion of the acid from solution in the next process step. In the preferred embodiments of this invention, the amount of water in the acid is sufficiently low that the above described result is obtained. As was noted above, the first and second steps can be combined and an amount of acid sufficient to adjust the pH of the mixture and provide sufficient anions can be added prior to or during reduction. Illustrative of suitable acid species are HCl, $H_2SO_4$, HI, $H_2CO_3$, $H_3PO_4$, HF, HBR, $H_2ClO_4$ and the like. The preferred acid species are HCl, HBR, HF and HI and amongst these preferred acid species, HCl is particularly preferred for use in the invention primarily because chromic halides in general and chromic chloride in particular are commercially of most importance. The acid can also be added to the reaction mixture by addition of a compound or mixture by reaction with water in situ. For example, such species as sulfur trioxide, phosphorous pentoxide, carbon dioxide, nitrous oxide and the like can be added to the aqueous reaction mixture to form sulfuric acid, phosphoric acid, carbonic acid and nitric acid, respectively, in situ.

The amount of acid employed should be sufficient to adjust the pH of the reaction misture as desired, and to provide a sufficient amount of counter ions. The amount of counter ion required is dependent on the valency of the counter ion, and on the amount of chromium and sodium ions in the reaction mixture. In the preferred embodiments of this invention at least a stiochiometric amount of the acid, based on the ratio of equivalents of counter ion to total equivalents of $Cr^{+3}$ and other cations reduction step is employed, and in the particularly pre- Reduction reaction temperatures are not critial and can vary from −15° or lower up to about 100° C. or to the boiling point of the aqueous reaction mixture. For convenience, the reaction is usually carried out at room temperature. However, in those instances where reaction times are slow, higher temperatures can be used to provide increased rates of reaction. Reaction pressures are also not critical, and sub-atmospheric, atmospheric and super atmospheric pressures can be employed. Here again for convenience, the reduction reaction is usually carried out at autogenous pressure.

Reaction times can vary from instantaneous to one or more days, depending on such factors as the effectiveness of the particular reducing agent employed, reaction temperatures and like factors. Usually, the reaction will occur within about 2 to 3 seconds to about 3 to 4 hours after contacting the reactants.

After completion of the reduction reation and addition of a stiochiometric amount of acid, the reaction mixture is cooled which results in preferential crystallization of substantially all of the salt of the chromate and/or dichromate counter-ion and the anion of the acid from the reaction mixture. In the preferred embodiments of the invention, the mixture is cooled to a temperature below about 25° C., and in the particularly preferred embodiments the mixture is cooled to a temperature below about 10° C. Amongst these particularly preferred embodiments, most preferred are those embodiments in which the reaction mixture is cooled to a temperature of between about 0° C. and about 10° C. The crystallized salt can be conveniently separated from the reaction mixture by such conventional separation procedures as centrifugation, filtration and the like to provide an aqueous solution of $Cr^{+3}X^{-m}{}_{n/2}$ containing substantially no cations. In the preferred embodiments of the invention, the amount of said cations is less than about 3 weight percent based on the total weight of the crystals and in the particularly preferred embodiments is less than about 2 weight percent of the chromate and/or dichromate precur sors. Most preferred are those embodiments in which the amount of said cation is less than about 1 weight percent. Useful separation procedures, and apparatuses for practicing same are well known in the art and will not be described herein in great detail.

Solid $Cr^{+3}X^{-m}{}_{n/2}$ can be conveniently recovered from the aqueous product merely by conventional crystallization techniques. For example, a precipitating effective amount of the water, which is defined herein as an amount of water sufficient to allow preferential crystallization of the $Cr^{+3}X^{-m}{}_{n/2}$ species in the solution, can be removed from the system by any convenient technique, as for example by boiling the system at atmospheric or reduced pressures. After removal of a sufficient amount of water, the reaction mixture can be cooled and crystallized $Cr^{+3}X^{-m}{}_{n/2}$ can be recovered employing procedures substantially identical to those used to separate the salt of the chromate and/or dichromate counter-ion and the anion of the acid from the aqueous solution in the prior step.

$Cr^{+3}X^{-m}{}_{n/2}$ salts prepared in accordance with this process have many and varied uses well-known to those of skill in the art. For example, one such species, chromic chloride, can be used as a precursor in the manufacture of catalysts, chromium metal and organic compounds of chromium. Chromic chloride can also be used in an efficient fuel cell recently developed by NASA.

The following specific examples are presented to more particularly illustrate the invention.

EXAMPLE I

Preparation of Chromic Chloride

Sodium chromate (100 grams) was dissolved in a mixture of 78 grams of $H_2O$ and 63 grams of 36% HCl. To this solution about 20 grams of 99.3% methyl alcohol was slowly added. The solution was then transferred to a 500 mL capacity gas washing bottle. The temperature of the system was lowered to about 8°-10° C. and maintained there by use of an ice bath. Into the bottle a stiochiometric amount of anhydrous hydrogen chloride gas was introduced. Upon completion of hydrogen chloride gas introduction, the temperature in the inside of gas washing bottle was 14° C. and the solution, in the gas washing bottle, was a thick slurry. The slurry was filtered through a fritted glass filter. The crystals recovered were almost crystalline, and were contaminated with very little green color which indicate essentially no chromic (+3) chloride had crystallized. The crystals which were identified as sodium chloride were recovered m about 95.5% of the theoretical yield. The volume of the filtrate collected was about 297 mL. The filtrate which contained chromic chloride was boiled which concentrated it to a total volume of about 120 mL. This concentrated chromic chloride solution was cooled in air to a temperature of about 30° C. which resulted in precipitation of chromium chloride thereby forming a slurry. The slurry of chromic chloride was filtered through a fritted glass filter. The recovered chromium chloride weighed about 119 grams which was about 72.3% of the theoretical yield. The recovered chromic chloride hexahydrate was analyzed and contained only about 2.06% $Na^+$.

EXAMPLES II TO X

Preparation of Chromic Chloride

Employing the procedure of EXAMPLE I, a wide variety of reducing agents can be employed in the preparation of chromic chloride as set forth in the following TABLE I.

TABLE I

| EX | Sodium Chromate | $H_2O$ | 36% HCl | Reducing Agent |
|---|---|---|---|---|
| II | 100 gm | 78 gm | 63 gm | 86 gm of formic acid |
| III | 200 gm | 156 gm | 126 gm | 60 gm of formaldehyde |
| IV | 100 gm | 78 gm | 63 gm | 60 gm of hydrogen peroxide |
| V | 50 gm | 39 gm | 37.5 gm | 26.5 gm of carbon monoxide |
| VI | 25 gm | 19.5 gm | 15.78 gm | 33.78 gm of hydrogen chloride |
| VII | 200 gm | 156 gm | 125 gm | 226 gm of i-propanol |
| VIII | 75 gm | 58.5 gm | 47.5 gm | 64.5 gm of ethanol |
| IX | 50 gm | 39 gm | 31.5 gm | 9 gm of sodium borohydride |
| X | 25 gm | 11.5 gm | 15.78 gm | 1 gm of hydrogen |

After reaction of the reagents listed in Table I, anhydrous hydrogen chloride can be introduced into the reaction mixture to form chromic chloride in accordance with the procedure of Example I.

EXAMPLE XI

Preparation of Chromic Sulfate

Into a reaction vessel fitted with a condensor and an addition funnel is charged 100 grams of potassium chromate, 78 grams of $H_2O$ and 15 grams of 98% $H_2SO_4$. To this solution about 20 grams of 99.3% methyl alcohol is slowly added. The reaction vessel is placed in an ice bath and the temperature of the system is lowered to about 8°–10° C. On standing, the solution is transformed into a thick potassium chloride slurry. The slurry which is filtered through a fritted glass filter and the recovered filtrate is concentrated by boiling. This concentrated chromic sulfate solution is cooled in air to temperature of about 30° C. crystallizing the chromic sulfate and is then filtered through a fritted glass filter to collect the chromium sulfate crystals.

EXAMPLE XII

Preparation of Chromic Nitrate

Into a reaction vessel fitted with a condensor and an addition funnel is charged 100 grams of sodium chromate and 63 grams of 29% $HNO_3$. To this solution about 20 grams of 99.3% methyl alcohol is added slowly. The reaction vessel is placed in an ice bath and the temperature of the system is lowered to about 8°–10° C. On standing, the solution becomes a thick sodium nitrate slurry. The slurry is filtered through a fritted glass filter, and the filtrate is concentrated by boiling. This concentrated chromic nitrate solution is cooled in air to a temperature of about 30° C. crystallizing the chromic nitrate to form another slurry. The chromic nitrate slurry is filtered through a fritted glass filter to collect the chromic nitrate crystals.

EXAMPLE XIII

Preparation of Chromic Bromide

Into a reaction vessel fitted with a condensor and an addition funnel is charged 100 grams of calcium chromate, 78 grams of $H_2O$ and 140 grams of 36% HBr. To this solution about 20 grams of 99.3% methyl alcohol is added slowly. The reaction vessel is then placed in an ice bath and the temperature of the system is lowered to 8°–10° C. On standing, the solution is transformed into a thick calcium bromide slurry. The slurry is filtered through a fritted glass filter and the filtrate is concentrated by boiling. This concentrated chromic bromide solution is cooled in to a temperature of 30° C., crystallizing the chromic bromide forming a slurry. The chromic bromide slurry is then filtered through a fritted glass filter to recover the crystallized chromic bromide.

EXAMPLE XIV

Preparation of Chromic Fluoride

Into a polyethylene reaction vessel fitted with a condensor and an addition funnel is charged 100 grams of sodium chromate, 78 grams of $H_2O$ and 35 grams of 36% aqueous HF. To this mixture about 20 grams of 99.3% methyl alcohol is added slowly. This solution is transferred to a 500 mL capacity polyethylene washing bottle and the temperature of the system is lowered to about 8°–10° C. under an ice bath. To this bottle a stiochiometric amount of anhydrous HF gas is introduced. Upon completion of HF gas injection, the solution in the gas washing bottle is transformed into a thick sodium fluoride slurry. This slurry is filtered through a stainless steel fritted filter and the slurry filtrate is concentrated by boiling. The concentrated chromic fluoride solution is cooled in air to a temperature of about 30° C., crystallizing the chromic fluoride forming another slurry which is filtered through a stainless steel fritted filter to recover the chromic fluoride crystals.

EXAMPLE XV

Preparation of Chromic Acetate

Into a reaction vessel fitted with a condensor and an addition funnel is charged 100 grams of sodium chromate, 78 grams of $H_2O$ and 130 grams of glacial acetic acid. To this mixture about 90 grams of 95% ethyl alcohol is added slowly. The reaction vessel is placed in an ice bath and the temperature of the system is lowered to about 8°–10° C. The solution in the reaction vessel becomes a thick slurry of sodium acetate. The slurry is filtered through a fritted glass filter. The collected filtrate is concentrated by boiling, and is cooled to a temperature of about 30° C. forming a chromic acetate slurry. The chromic acetate slurry is filtered through a fritted glass filter to recover chromic acetate crystals.

EXAMPLE XVI

Preparation of Chromic Phosphate

Into a reaction vessel fitted with a condensor and an addition funnel is charged 100 grams of barium chromate, 78 grams of $H_2O$ and 183 grams of 98% $H_3PO_4$. To this mixture about 20 grams of 99.3% methyl alcohol is added slowly. The reaction vessel is placed in an ice bath and the temperature of the system is lowered to about 8°–10° C. The solution in the reaction vessel is converted into a thick barium phosphate slurry, which is filtered through a fritted glass filter. The filtrate is collected and concentrated by boiling. This concentrated chromic phosphate solution is cooled in air to a temperature of about 30° C. to form a chromic phosphate slurry. The chromic phosphate slurry is filtered through a fritted glass filter to recover chromic phosphate crystals.

EXAMPLE XVII

Preparation of Chromic Iodide

Into a reaction vessel fitted with a condensor and an addition funnel is charged 100 grams of calcium chromate, and 840 grams of 47% HI. To this solution about 20 grams of 99.3% methyl alcohol can be added slowly. The reaction mixture is concentrated and the temperature of the system is lowered to about 8°–10° C. in an ice bath forming a calcium iodide slurry. The slurry is filtered through a fritted glass filter and the filtrate and calcium iodide crystals collected. The filtrate is concentrated by boiling and is cooled in air to a temperature of about 30° C. forming a chromic iodide slurry. The chromic iodide slurry is filtered through a fritted glass filter to recover chromic iodide crystals.

What is claimed is:

1. A process for preparing chromium (III) salts of the formula:

$$Cr^{+3} \cdot X^{-m}{}_{n/2}$$

from an Alkali metal or Alkaline Earth metal chromate and/or dichromate or a mixture thereof, wherein;
 X is halide;
 m is 1; and
 n is 6;

said process comprising the steps of:
- (A) forming a reaction mixture comprising one or more of the said chromate and/or dichromate salts, water, a reducing effective amount of reducing agent, and at least a stoichiometric amount of an acid or the formula $H_mX^{-m}$, and reacting said mixture for a time and at a temperature sufficient for chromium species in the +6 oxidation state to be reduced to the +3 oxidation state;
- (B) adding to said mixture of step (A) an acid identical to that used in step (A), or an anhydrous species capable of forming such acid in situ in an amount such that said mixture contains an amount of said acid equal to or greater than the amount of $Cr^{+3}$ and Alkali metal or Alkaline Earth metal in said mixture;
- (C) cooling said reaction mixture thereby selectively precipitating salt of said Alkali metal or Alkaline Earth metal and the anion of said acid from said reaction mixture; and
- (D) separating said precipitated salt from said reaction mixture thereby forming an aqueous solution of $Cr^{+3} \cdot X^{-m}{}_{n/2}$.

2. A process according to claim 1 wherein said reducing agent is methanol.

3. A process according to claim 1 wherein the chromate and/or dichromate salts are salts of Alkali metals.

4. A process according to claim 3 wherein said chromate and/or dichromate salts are salts of sodium.

5. A process of preparing chromium (III) salts of the formula:

$$Cr^{+3}X^{-m}{}_{n/2}$$

from chromate and/or dichromate salts, wherein;
X is a univalent, divalent or trivalent anion;
m is 1, 2 or 3; and
n is 2 when m is 3, n is 3 when m is 2, and n is 6 when m is 1; said process comprises the steps of:
- (A) forming a reaction mixture comprising said chromate and/or dichromate salts, water, a reducing effective amount of a reducing agent and at least a stoichiometric amound of an acid of the formula $H_mX^{-m}$, and reacting said mixture for a time and at a temperature sufficient for substantially all chromium species in the +6 oxidation state to be reduced to the +3 oxidation state;
- (B) adding to said mixture of step (A) an acid identical to that used in step (A), or an anhydrous species capable of forming such acid in situ in an amount such that said mixture contains an amount of said acid equal to or greater than the amount of $Cr^{+3}$ and other cations in said mixture;
- (C) cooling said reaction mixture thereby selectively precipitating salt of the chromate or dichromate counter ion and anion of said acid from said reaction mixture; and
- (D) separating said precipitated salt from said reaction mixture thereby forming an aqueous solution of $Cr^{+3}X^{-m}{}_{n/2}$.

6. A process according to claim 5 which further comprises the steps of removing water from said aqueous solution of step (D), cooling said solution to a temperature sufficient to cause preferential precipitation of $Cr^{+3}X^{-m}{}_{n/2}$; and separating said precipitated $Cr^{+3} \cdot X^{-m}{}_{n/2}$ from said solution.

7. A process according to claim 6 wherein said reducing agent is selected from the group consisting of reducing agents whose oxidative products are gases.

8. A process according to claim 7 wherein said reducing agents are selected from the group consisting of methanol, formaldehyde, formic acid, carbon monoxide and peroxide.

9. A process according to claim 8 wherein said reducing agent is methanol.

10. A process according to claim 8 wherein said salts are salts of sodium.

11. A process according to claim 5 wherein at least a stiochiometric amount of said reducing agent is employed.

12. A process according to claim 5 wherein $H_mX^{-m}$ is selected from the group consisting of HCl, $H_2SO_4$, $H_2CO_3$, HI, $H_3PO_4$, HF, HBr, and $H_2ClO_4$.

13. A process according to claim 5 wherein the amount of $H_mX^{-m}$ is sufficient to provide sufficient $X^{-m}$ counter-ion for $Cr^{+3}$ and other cations in the reaction mixture.

14. A process according to claim 13 wherein $H_mX^{-m}$ is selected from the group consisting of HF, HCl, HBr and HI.

15. A process according to claim 14 wherein $H_mX^{-m}$ is HCl.

16. A process according to claim 5 wherein said saturated reaction mixture is cooled to a temperature of between about 0° C. and about 25° C.

17. A process according to claim 5 wherein said acid is hydrogen chloride, said reducing agent is methanol, formaldehyde or formic acid and said chromate and/or dichromate salts are salts of alkali or alkaline earth metals.

18. A process according to claim 17 wherein said reducing agent is methanol.

19. A process according to claim 17 wherein said salts are salts alkali earth metals.

* * * * *